(12) United States Patent
Barrett et al.

(10) Patent No.: US 6,455,057 B1
(45) Date of Patent: *Sep. 24, 2002

(54) SKIN CARE COMPOSITION

(75) Inventors: Karen Elizabeth Barrett, Bedford (GB); Martin Richard Green, Bedford (GB); Heng-Long Hu, Gloucester (GB); Preyesh Parmar, Bedford (GB); Jonathan Richard Powell, Bedford (GB); Anthony Vincent Rawlings, Wirral (GB)

(73) Assignee: Elizabeth Arden Co., div. of Conopco, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/628,737

(22) Filed: Jul. 28, 2000

(30) Foreign Application Priority Data

Jul. 30, 1999 (GB) ............................................. 9918030

(51) Int. Cl.⁷ ................................................. A61K 7/00
(52) U.S. Cl. ....................... 424/401; 514/553; 514/554; 514/557; 514/844
(58) Field of Search .......................... 424/401; 511/553, 511/554, 557, 844

(56) References Cited

U.S. PATENT DOCUMENTS 6,042,841 A * 3/2000 Alaluf et al. ............... 424/401
6,099,591 A * 8/2000 Matravers et al. ............. 8/408

FOREIGN PATENT DOCUMENTS

| EP | 709 084 | 5/1996 |
|---|---|---|
| EP | 1 013 178 | 6/2000 |
| JP | 0 116 439 A2 * | 8/1984 |
| JP | 0 116 439 A2 * | 9/1984 |
| JP | 05/271046 * | 10/1993 |
| JP | 07/277 939 | 10/1995 |
| WO | 96/37201 | 11/1996 |

OTHER PUBLICATIONS

Great Britain Search Report in a GB application 9918030.9.
PCT International Search Report in a PCT application PCT/EP 00/06596.
Derwent Abstract of JP 05 271046—published Oct. 19, 1993.

* cited by examiner

Primary Examiner—Jose G. Dees
Assistant Examiner—Konata M. George
(74) Attorney, Agent, or Firm—Ellen PLotkin

(57) ABSTRACT

A topical composition comprising:
  (a) petroselinic acid and/or derivatives thereof;
  (b) a phenolic compound and/or mixtures thereof; and
  (c) a dermatologically acceptable vehicle.

The product is particularly useful for treating wrinkles and soothing sensitive skin.

7 Claims, No Drawings

SKIN CARE COMPOSITION

FIELD OF THE INVENTION

This invention relates to topical compositions for application to human skin and to their use in improving the condition and appearance of skin.

BACKGROUND OF THE INVENTION

Skin is subject to deterioration through dermatological disorders, environmental abuse (wind, air conditioning, and central heating) or through the normal aging process (chronoageing) which may be accelerated by exposure of skin to sun (photoageing). In recent years the demand for cosmetic compositions and cosmetic methods for improving the appearance and condition of skin has grown enormously.

Consumers are increasingly seeking "anti-ageing" cosmetic products that treat or delay the visible signs of chronoageing and photoageing skin such as wrinkles, lines, sagging, hyperpigmentation and age spots.

Consumers also frequently seek other benefits from cosmetic products in addition to anti-ageing. The concept of "sensitive skin" has also raised the consumer demand for cosmetic products that improve the appearance and condition of sensitive, dry and/or flaky skin and to soothe red, and/or irritated skin. Consumers also desire cosmetic products that have an oil/sebum control effect.

Many people are concerned with the degree of pigmentation of their skin. For example, people with age spots or freckles may wish such pigmented spots to be less pronounced. Others may wish to reduce the skin darkening caused by exposure to sunlight or to lighten their natural skin colour. To meet this need many attempts have been made to develop products that reduce the pigment production in the melanocytes. However, the substances thusfar identified tend to have undesirable side effects, e.g. skin irritation.

Consequently such substances are not suitable for cosmetic use or they can only be applied at a concentration at which their skin lightening effect is less than desired. Using a combination of different skin lightening substances may be considered to reduce adverse side effects but there is a substantial risk that by using such a combination the skin lightening is reduced as well due to competition effects. Therefore there is a need for improvement in the effectiveness of cosmetic skin lightening products particularly, such that they do not irritate the skin.

J07277939 describes a skin care composition for improving skin ageing and skin inflammation that contains (A) Flor de Manita and (B) at least 1 of active selected from oxygen removers, antioxidants, cell activators, anti-inflammatories, tyrosinase inhibitors and moisture-retaining agents. Amongst the many options of ingredients described for component B are quercetin, quercitolin, catechin, gallic acid, gamma-linolenic acid, and eicosapentaenoic acid.

J05271046 describes a skin lightening composition that contains an unsaturated fatty acid having 18 to 22 carbons and two or more unsaturated bonds, such as linoleic and arachidonic acid, and a polyphenol.

Use of oils rich in petroselinic acid in skin care compositions as a moisturising agent has been described in EP A 0709084.

The use of fatty acids, including petroselinic acid, in cosmetic formulations for treating the hair is known. EP-A-116439 describes hair tonics, which include fatty acids, (such as petroselinic acid, for alleviating dandruff and itch and for stimulating hair growth.

However, the art discussed above does not disclose the specific synergistic combination of petroselinic acid with a phenolic compound nor the use of such a specific combination for treating wrinkles, sensitive skin, dry skin, controlling oil/sebum secretion, or lightening skin.

We have now found that effective treatment and prevention of normal, but cosmetically undesirable, skin conditions, due to chronoageing or photoageing, such as wrinkles, lines, sagging, hyperpigmentation and age spots, may be-obtained through the application of cosmetic compositions to the skin which comprise a specific fatty acid - petroselinic acid and/or derivatives thereof, in combination with a phenolic compound. We have also found that the use of such cosmetic compositions advantageously provides further skin care benefits in addition to anti-ageing such as soothing sensitive and/or irritated skin, controlling oil/sebum secretion and for lightening the skin.

SUMMARY OF THE INVENTION

According to a first aspect of the present invention there is provided a topical composition comprising:
  (a) petroselinic acid and/or derivatives thereof;
  (b) a phenolic compound and/or mixtures thereof; and
  (c) a dermatologically acceptable vehicle.

According to a second aspect of the present invention there is provided a cosmetic method of providing at least one skin care benefit selected from: treating/preventing wrinkling, sagging, dry aged and/or photodamaged skin; boosting collagen deposition in skin, boosting decorin production in skin, enhancing tissue repair; soothing irritated, red and/or sensitive skin; improving skin texture, smoothness and/or firmness; lightening skin; controlling oil/sebum secretion the method comprising applying to the skin a topical composition as described above.

The present invention also encompasses the use of the inventive compositions for providing at least one skin care benefit selected from treating/preventing wrinkling, sagging, aged and/or photodamaged skin; boosting collagen deposition in skin, boosting decorin production in skin, enhancing tissue repair; soothing irritated, red and/or sensitive skin; improving skin texture, smoothness and/or firmness; lightening skin; controlling oil/sebum secretion.

According to a still further aspect of the present invention there is provided the use of petroselinic acid and/or derivatives thereof in combination with a phenolic compound and/or mixtures thereof in a cosmetic topical composition for providing at least one cosmetic skin care benefit selected from treating/preventing wrinkling, sagging, aged and/or photodamaged skin; boosting collagen deposition in skin, boosting decorin production in skin, enhancing tissue repair; soothing irritated, red and/or sensitive skin; improving skin texture, smoothness and/or firmness; lightening skin; and controlling oil/sebum secretion.

The inventive compositions, methods and uses thus provide anti-aging benefits which result in the promotion of smooth and supple skin with improved elasticity and a reduced or delayed appearance of wrinkles and aged skin, with improved skin colour. A general improvement in the appearance, texture and condition, in particular with respect to the radiance, clarity, and general youthful appearance of skin is achieved. The inventive compositions, methods and uses are also beneficial for soothing and calming sensitive and/or irritated skin, for lightening skin and for controlling oil/sebum secretion. Thus the present invention advantageously provides a wide range of skin care benefits.

The term "treating" as used herein includes within its scope reducing, delaying and/or preventing the above mentioned normal skin conditions such as wrinkled, aged, and/or photodamaged, and/or irritated skin and generally enhancing the quality of skin and improving its appearance and texture by preventing or reducing irritation, wrinkling and increasing flexibility, firmness, smoothness, suppleness and elasticity of the skin. The compositions, methods and uses according to the invention may be useful for treating skin which is already in a wrinkled, aged, photodamaged, irritated condition or for treating youthful skin to prevent or reduce those aforementioned undesirable changes due to the normal aging/photoaging process.

DETAILED DESCRIPTION OF THE INVENTION

Petroselinic Acid

Petroselinic acid (hereinafter referred to as PA) is a monounsaturated long chain (C18) fatty acid, having the formula $CH_3(CH_2)_{10}CH=CH(CH_2)_4COOH$.

The invention also includes derivatives of the free acid which thus comprise petroselinic acid moieties. Preferable derivatives include those derived from substitution of the carboxyl group of the acid, such as esters (e.g. triglyceride esters, monoglyceride esters, diglyceride esters, phosphoesters), amides (e.g. ceramide derivatives), salts (eg alkali metal and alkali earth metal salts, ammonium salts); and/or those derived from substitution of the C18 carbon chain, such as alpha hydroxy and/or beta hydroxy derivatives.

In the case of triglyceride ester derivatives, all positional isomers of PA substituents on the glycerol backbone are included. The triglycerides must contain at least one PA moiety. For example, of the three esterifiable positions on the glycerol backbone, the 1 and 2 positions may be esterified with PA and by another lipid at position 3 or as an alternative, the glycerol backbone could be esterified by PA at the 1 and 3 positions with another lipid at position 2.

Oils that are rich in petroselinic acid triglyceride are thus also suitable for use in the present invention. Such oils are commercially available and include parsley seed oil, carrot seed oil, fennel fruit oil, parsnip seed oil, coriander seed oil, chervil seed oil, caraway plant oil, and celery seed oil.

Wherever the term "petroselinic acid" or "PA" is used in this specification it is to be understood that the derivatives thereof comprising PA moieties are also included. "PA moieties" refers to PA fatty acyl portion(s) of a PA derivative.

The PA to be employed in accordance with the present invention is present in the topical composition in an effective amount. Normally the total amount of the active is present in an amount between 0.0001% and 50% by weight of the composition. More preferably the amount is from 0.01% to 10% and most preferably from 0.1% to 5% in order to maximise benefits at a minimum cost.

Phenolic Compounds

Phenolic compounds can be divided into at least 10 different classes depending on their basic chemical structure. The compounds include simple phenols ($C_6$), benzoquinones ($C_6$), phenolic acids ($C_6-C_1$), acetophenones ($C_6-C_2$), phenylacetic acids ($C_6-C_2$), hydroxycinnamic acids ($C_6-C_3$), phenylpropenes ($C_6-C_3$), coumarins, isocoumarins ($C_6-C_3$), chromones ($C_6-C_3$), naftoquinones ($C_6-C_4$), xanthones ($C_6-C_1-C_6$), stilbenes ($C_6-C_2-C_6$), flavonoids ($C_6-C_3-C_6$), lignans, neolignans ($C_6-C_3)_2$ and lignins ($C_6-C_3)_n$.

The term flavonoids represent a very large group of compounds consisting of two aromatic rings joined by a three-carbon unit, e.g. $C_6-C_3-C_6$. The family of flavonoids includes isoflavonoids monomeric flavonols, dihydroflavonoids, catechins, epicatechins (e.g. laurones), leucoanthocyanadins, proanthocyanadins, anthocyanadins, flavones, flavonones, chalcones, dihydrochalcones, isoflavones, neoflavones, aurones, flavan 3 ols, flavon 3 ols, and antrocyanins. The term isoflavanoids also includes isoflavones, pterocarpans, isoflavonones, retenoids, isoflavans and isoflavanols.

The preferred phenolic compounds for use in the compositions of the present invention are flavonoids including flavonones such as naringenin, flavonols such as quercetin, catechin (e.g. epigallocatechingallate, EGCG), isoflavonoids such as daidzein, genistein, lycetin, and also phenolic acids, such as gallic acid, and the green tea polyphenols.

Quercetin, naringenin, daidzein, genistein, EGCG and green tea polyphenols may be obtained from Sigma. Plant extracts containing the phenolic compounds are also suitable for use in the present invention. For example, rutin, evening primrose, onion, citrus species contain quercetin and naringenin, soy contains daidzin and genistein and green tea varieties such as Camellia sinensis and assamica contain EGCG and green tea polyphenols.

The phenolic compound or mixtures thereof is employed in the inventive composition in an amount of from about 0.01% to about 10%, preferably in an amount of from about 10% to about 1%, most preferably in an amount of from about 0.1% to about 5%.

Dermatologically Acceptable Vehicle

The composition used according to the invention also comprises a dermatologically/cosmetically acceptable vehicle to act as a dilutant, dispersant or carrier for the actives. The vehicle may comprise materials commonly employed in skin care products such as water, liquid or solid emollients, silicone oils, emulsifiers, solvents, humectants, thickeners, powders, propellants and the like.

The vehicle will usually form from 5% to 99.9%, preferably from 25% to 80% by weight of the composition, and can, in the absence of other cosmetic adjuncts, form the balance of the composition.

Optional Skin Benefit Materials and Cosmetic Adjuncts

Besides the actives, other specific skin-benefit actives such as sunscreens, skin-lightening agents, skin tanning agents may also be included. The vehicle may also further include adjuncts such as antioxidants, perfumes, opacifiers, preservatives, colourants and buffers.

Product Preparation, Form, Use and Packaging

To prepare the topical composition used in the method of the present invention, the usual manner for preparing skin care products may be employed. The active components are generally incorporated in a dermatologically/cosmetically acceptable carrier in conventional manner. The active components can suitably first be dissolved or dispersed in a portion of the water or another solvent or liquid to be incorporated in the composition. The preferred compositions are oil-in-water or water-in-oil or water-in-oil-in-water emulsions.

The composition may be in the form of conventional skin-care products such as a cream, gel or lotion, capsules or the like. The composition can also be in the form of a so-called "wash-off" product e.g. a bath or shower gel, possibly containing a delivery system for the actives to promote adherence to the skin during rinsing. Most preferably the product is a "leave-on" product; a product to be applied to the skin without a deliberate rinsing step soon after its application to the skin.

The composition may packaged in any suitable manner such as in a jar, a bottle, tube, roll-ball, or the like, in the conventional manner. It is also envisaged that the inventive compositions could be packaged as a kit of two separate compositions one containing the petroselinic acid and the second containing the phenolic compound, to be applied to the skin simultaneously or consecutively.

The composition according to the invention may also be formulated into a form suitable for oral ingestion such as a capsule, tablet or similar.

The method of the present invention may be carried out one or more times daily to the skin which requires treatment. The improvement in skin appearance will usually become visible after 3 to 6 months, depending on skin condition, the concentration of the active components used in the inventive method, the amount of composition used and the frequency with which it is applied. In general, a small quantity of the composition, for example from 0.1 to 5 ml is applied to the skin from a suitable container or applicator and spread over and/or rubbed into the skin using the hands or fingers or a suitable device. A rinsing step may optionally follow depending on whether the composition is formulated as a "leave-on" or a "rinse-off" product.

In order that the present invention may be more readily understood, the following examples are given, by way of illustration only.

EXAMPLES

Example 1

Procedure for Measuring Procollagen-I and Decorin Synthesis in Human Dermal Fibroblasts
Preparation of Dermal Fibroblast Conditioned Medium Primary human foreskin fibroblasts at passage 2 (P2) were seeded into 12-well plates at 10000 cells/cm$^2$ and maintained for 24 hours in an atmosphere of 5% carbon dioxide and 4% oxygen in Dulbeccos Modified Eagles Medium (DMEM) supplemented with 10% foetal calf serum. After this time the cells were washed with serum free DMEM and then incubated in fresh serum free DMEM for a further 60 hours. The fibroblast monolayers were then washed again with serum free DMEM. Test reagents and vehicle controls were added to the cells in triplicate in a final volume of 0.4 ml/well fresh serum free DMEM and incubated for a further 24 hours. This fibroblast conditioned medium was either analysed immediately or snap frozen in liquid nitrogen and stored at −70° C. for future analysis. The cells were then counted and data from the dot-blot analysis subsequently standardised to cell number.

Example 2

Dot Blot Assay for Procollagen-I and Decorin Protein in Dermal Fibroblast Conditioned Medium Samples of conditioned medium from dermal fibroblasts treated with vehicle (as a control) or test reagents were supplemented with 20 mM dithiothreitol (1:10 dilution of 200 mM stock solution) and 0.1% sodium dodecylsulphate (1:100 dilution of 10% stock solution), mixed well and then incubated at 75° C. for 2 minutes. A standard for the assay was generated by serial dilution of neat fibroblast conditioned medium from fibroblasts seeded at 10000 cells/cm$^2$ in a 175 cm$^2$ flask and maintained in serum free DMEM as described above.

Assay samples were subsequently applied in triplicate to a prewetted sheet of Immobilon-P transfer membrane using the 96-well Bio-Dot Apparatus from Bio-Rad as described in the manufacturers guidelines. Approximately 200 μl of medium was applied per well. The medium was allowed to filter through the membrane under gravity (30 minutes) after which the membrane was washed twice with PBS (200 μl). These PBS washes were allowed to filter through the membrane under gravity (2×15 minutes). The Bio-Dot apparatus was then attached to a vacuum manifold and a third and final PBS wash carried out under suction. The apparatus was disassembled, the membrane removed and quickly cut as required before being placed in blocking buffer overnight at 4° C. Membranes prepared for decorin analysis were blocked with 3% (w/v) BSA/0.1% (v/v) Tween 20 in PBS, whilst those for procollagen-I analysis were blocked with 5% (w/v) non fat dried milk powder/0.05% Tween 20 in PBS. The following day, the membranes were probed with 1:10000 dilution of primary antibodies to either human procollagen-I (MAB1912; rat monoclonal; Chemicon Int. Inc., Temecula, Calif.) or human decorin (rabbit polyclonal; Biogenesis) for 2 hours at room temperature.

The membranes were subsequently washed with TBS/ 0.05% Tween 20 (3×5 minutes) and then incubated with 1:1000 dilution of $^{125}$I-conjugated anti-rat or anti-rabbit F(ab')2 fragments (Amersham) as required for 1 hour at room temperature. Following this the Immobilon strips were again washed with TBS/Tween 20 (3×5 minutes) before being allowed to dry in air at room temperature. The dried membranes were wrapped in cellophane and exposed to a Molecular Dynamics storage phosphor screen for 16–18 hours. At the end of this time the exposed screen was scanned by a phosphorimager (Molecular Dynamics Phosphorimager SF) using ImageQuant™ software. Dot intensity was assessed by computer-assisted image analysis using the quantification tools in ImageQuant™, standardised to cell number and the effects of various test reagents on decorin and procollagen-I synthesis were determined relative to a vehicle treated control value of 100 arbitrary units.

Example 3

TESTS

The table 1 below indicates the synergistic effect of petroselinic acid in combination with the phenolic compounds epigallocatechin gallate (EGCG), gallic acid, diadzein, genestein, quercetin on procollagen-I and/or decorin synthesis in human dermal fibroblasts, and the amounts in which the actives were applied. In order to normalise the results the effects of the test substances were determined relative to a vehicle treated control value of 100 arbitrary units. The concentrations of reagents used in the trials had no influence on cell viability. The differences in percentage values for 0.01 micromolar petroselinic acid observed between experiments reflects the normal variation between experiments, including that arising from the use of different cell lines.

TABLE 1

| Treatment | Procollagen-I | Decorin |
|---|---|---|
| Control (Vehicle) | 100 | 100 |
| 0.01 µM PA | | 93.7% |
| 0.005 µg/ml EGCG | | 118.4% |
| 0.01 µM PA + 0.005 µg/ml EGCG | | 140.5% |
| 0.01 µM PA | | 91.6% |
| 0.05 µg/ml EGCG | | 111.7% |
| 0.01 µM PA + 0.05 µg/ml EGCG | | 131.2% |
| 0.01 µM PA | | 102.7% |
| 0.5 µg/ml EGCG | | 120.2% |
| 0.01 µM PA + 0.5 µg/ml EGCG | | 155.9% |
| 0.01 µM PA | | 100.9% |
| 0.001 µg/ml gallic acid | | 96.6% |
| 0.01 µM PA + 0.001 µg/ml gallic acid | | 129.2% |
| 0.1 µM PA | 90.94% | 100.3% |
| 0.01 µM daidzein | 96.04% | 92.83% |
| 0.1 µM PA + 0.01 µM daidzein | 132.3% | 136.29% |
| 0.01 µM PA | 117.34% | 95.08% |
| 1 µM genistein | 101.74% | 99.75% |
| 0.01 µM PA + 1 µM genistein | 130.23% | 125.41% |
| 0.01 µM PA | | 93.97% |
| 1 µM quercetin | | 97.60 |
| 0.01 µM PA + 1 µM quercetin | | 109.19% |

The results in table 1 indicate that the combination of petroselinic acid with a phenolic compound synergistically upregulates the synthesis of procollagen-I and/or decorin in human dermal fibroblasts.

The level of decorin in skin is associated with improved condition and appearance of skin. Increasing the level of decorin in skin is important for controlled and correct deposition of collagen in skin that is associated with many skin benefits such as wrinkle effacement and dermal repair of photodamaged skin.

Example 4

This example demonstrates the synergistic effect of the specific combination of petroselinic acid and a phenolic compound on reducing the inflammatory response of dermal fibroblasts.

Fibroblasts $PGE_2$ and ICAM Assay

Intracellular adhesion molecules (ICAM) and $PEG_2$ production by human skin fibroblasts can be induced by the inflammatory stimulus PMA (phorbal myristate acetate). PMA represents an external stressor which induces oxidative stress and inflammatory responses in cells. This model is used to model inflammation in vivo.

Primary human foreskin fibroblasts at passage 2 (P2) were seeded into 96-well plates at 10000 cells/well and maintained for 24 hours in an atmosphere of 5% carbon dioxide in Dulbeccos Modified Eagles Medium (DMEM) supplemented with 10% foetal calf serum. The test substances as indicated in the table 2 below were added to fresh cell media (DMEM, supplemented with 10% foetal calf serum) in dimethylsulphoxide and ethanol final concentration<1%) in triplicate and incubated for a further 24 hours. Phorbal myristate acetate (PMA) (Sigma) was added 10 nM to the media and the cells incubated for a further 24 hours. The control only contained the vehicle did not contain any test compounds or any PMA. The fibroblasts/media were then analysed as described below immediately or snap frozen in liquid nitrogen and stored at −70° C. for future analysis. The cells were then counted and data from the dot-blot analysis subsequently standardised to cell number.

Prostaglandin E2 ($PGE_2$) Assay:

Volumes of 50 µl culture medium were taken for $PGE_2$ assay after gently shaking the culture plate. $PGE_2$ levels in the medium were determined with a Biotrak $PGE_2$ immunoassay kit (Amersham, UK). The assay is based on the competition between unlabelled $PGE_2$ in the sample and a fixed quantity of horseradish peroxidase labelled $PGE_2$ for a limited amount of fixed $PGE_2$ specific antibody. Concentrations of unlabelled sample $PGE_2$ are determined according to a standard curve which was obtained at the same time.

ICAM-1 assay:

Media were discarded and cells washed with Dulbecco PBS. To the washed cells, 150 µl 0.1% Triton X-100 (Sigma) was added for 3 minutes to extract ICAM from cell membrane. The extracts were transferred to Eppendoff centrifuge tubes and centrifuged at 1000 g for 2 min to remove cell debris. A volume of 100 µl supernatant was used for ICAM assay. The soluble ICAM-1 was assessed with commercially available immunoenzymometric assay kit (R&D Systems). Concentrations of ICAM-1 in the samples were determined based on parallel running standard curve.

The results that were obtained from the $PGE_2$ and ICAM assay are summarised in table 2 below.

TABLE 2

| Treatment | % of Inhibition Of Fibroblast $PGE_2$ Levels | % of inhibition of fibroblast ICAM production |
|---|---|---|
| Control | 100 | 100 |
| PMA + PA 1 nM | | −5 |
| PMA + EGCG 10 µM | | 14.4 |
| PMA + PA 1 nM + EGCG 10 µM | | 56.1 |
| PMA + quercetin 10 µM | | 27.8 |
| PMA + PA 1 nM + quercetin 10 µM | | 48.3 |
| PMA + PA 1 nM | 27.26 | 25.91 |
| PMA + genistein 1 µM | 86.16 | 30.59 |
| PMA + PA 1 nM + genistein 1 µM | 51.98 | 63.79 |

The above results show that challenging cells with an inflammatory stimulus such as PMA (Phorbol myristyl acetate) causes an increase in the inflammatory response as measured by prostaglandin E2 ($PGE_2$) production. The specific combination of petroselinic acid and phenolic compound synergistically reduces the inflammatory response as measured by $PGE_2$ production. The results thus demonstrate that the specific combinations of actives within the scope of the present invention exhibit surprisingly synergistic anti-inflammatory activity.

The above results also demonstrate that challenging cells with PMA causes an increase in ICAM production. Treating the cells with a combination of petroselinic acid phenolic compound synergistically decreases the production of Intracellular adhesion molecule (ICAM), which is another marker of inflammation. These results thus further demonstrate that the specific combinations of actives within the scope of the present invention exhibit a good and surprisingly synergistic anti-inflammatory activity.

Example 5

The formulation below describes an oil in water cream suitable for the methods and uses according to the present invention. The percentages indicated are by weight of the composition.

|  | wt % | Wt % | Wt % |
| --- | --- | --- | --- |
| Mineral Oil | 4 | 4 | 4 |
| Petroselinic acid (triglyceride) ex Elysion | 1.15 | 2 | 3 |
| Green Tea Polyphenols | 0 | 2 | 0 |
| EGCG | 0 | 0 | 1 |
| Quercetin | 0.5 | 0 | 0 |
| Brij 56* | 4 | 4 | 4 |
| Alfol 16RD* | 4 | 4 | 4 |
| Triethanolamine | 0.75 | 0.75 | 0.75 |
| Butane-1,3-diol | 3 | 3 | 3 |
| Xanthan gum | 0.3 | 0.3 | 0.3 |
| Perfume | qs | qs | qs |
| Butylated hydroxy toluene | 0.01 | 0.01 | 0.01 |
| Water | to 100 | to 100 | to 100 |

*Brij 56 is cetyl alcohol POE (10)
Alfol 16RD is cetyl alcohol

Example 6

The formulation below describes an emulsion cream according to the present invention.

| FULL CHEMICAL NAME OR CTFA NAME | TRADE NAME | WT. % | WT. % | WT % |
| --- | --- | --- | --- | --- |
| Coriander seed oil ex Loders Croklaan (PA triglyceride 60–75% of total fatty acids) |  | 2.0 | 3 | 1.5 |
| Gallic acid |  | 1 | 0 | 0 |
| Genistein |  | 0 | 2 | 0 |
| Diadzein |  | 0 | 0 | 1.5 |
| Disodium EDTA | Sequesterene Na2 | 0.05 | 0.05 | 0.05 |
| Magnesium aluminium silicate | Veegum Ultra | 0.6 | 0.6 | 0.6 |
| Methyl paraben | Methyl Paraben | 0.15 | 0.15 | 0.15 |
| Simethicone | DC Antifoam Emulsion | 0.01 | 0.01 | 0.01 |
| Butylene glycol 1,3 | Butylene Glycol 1,3 | 3.0 | 3.0 | 3.0 |
| Hydroxyethylcellulose | Natrosol 250HHR | 0.5 | 0.5 | 0.5 |
| Glycerine, USP | Glycerine USP | 2.0 | 2.0 | 2.0 |
| Xanthan gum | Keltrol 1000 | 0.2 | 0.2 | 0.2 |
| Triethanolamine | Triethanolamine (99%) | 1.2 | 1.2 | 1.2 |
| Stearic acid | Pristerene 4911 | 3.0 | 3.0 | 3.0 |
| Propyl paraben NF | Propylparaben NF | 0.1 | 0.1 | 0.1 |
| Glyceryl hydrostearate | Naturechem GMHS | 1.5 | 1.5 | 1.5 |
| Stearyl alcohol | Lanette 18 DEO | 1.5 | 1.5 | 1.5 |
| Isostearyl palmitate | Protachem ISP | 6.0 | 6.0 | 6.0 |
| C12–15 alcohols octanoate | Hetester FAO | 3.0 | 3.0 | 3.0 |
| Dimethicone | Silicone Fluid 200 (50 cts) | 1.0 | 1.0 | 1.0 |
| Cholesterol NF | Cholesterol NF | 0.5 | 0.5 | 0.5 |
| Sorbitan stearate | Sorbitan Stearate | 1.0 | 1.0 | 1.0 |
| Butylated hydroxytoluene | Embanox BHT | 0.05 | 0.05 | 0.05 |
| Tocopheryl acetate | Vitamin E Acetate | 0.1 | 0.1 | 0.1 |
| PEG-100 stearate | Myrj 59 | 2.0 | 2.0 | 2.0 |
| Sodium stearoyl lactylate | Pationic SSL | 0.5 | 0.5 | 0.5 |
| Hydroxycaprylic acid | Hydroxycaprylic Acid | 0.1 | 0.1 | 0.1 |
| Alpha-bisabolol | Alpha-bisabolol | 0.2 | 0.2 | 0.2 |
| Water, DI |  | q.s. to 100 | q.s. to 100 | q.s. to 100 |

Both the above topical compositions of example 5 and 6 provide an effective cosmetic treatment to improve the appearance of wrinkled, aged, photodamaged, and/or irritated skin, when applied to normal skin that has deteriorated through the aging or photoageing or when applied to youthful skin to help prevent or delay such deteriorative changes. The compositions are also effective for soothing irritated skin, conditioning dry skin, lightening skin colour and reducing oil and sebum secretions. The compositions can be processed in conventional manner.

What is claimed is:

1. A topical skin care composition comprising:

(a) a petroselinic acid compound wherein petroselinic acid is found in a form selected from the group consisting of a free acid, an ester, an amide and a salt thereof;

(b) 0.01 to 10% by weight of a phenolic compound selected from the group consisting of benzoquinones ($C_6$), phenolic acids ($C_6$–$C_1$), Acetophenones ($C_6$–$C_2$), phenylacetic acids ($C_6$–$C_2$), hydroxycinnamic acids ($C_6$–$C_3$), phenylpropenes ($C_6$–$C_3$), coumarins, isocoumarins ($C_6$–$C_3$), chromones ($C_6$–$C_3$), naftoquinones ($C_6$–$C_4$), xanthones ($C_6$–$C_1$–$C_6$), stilbenes ($C_6$–$C_2$–$C_6$), flavonoids ($C_6$–$C_3$–$C_6$), lignans, neolignans ($C_6$–$C_3$)$_2$, lignins ($C_6$–$C_3$)$_n$ and/or mixtures thereof; and (c) a cosmetically acceptable vehicle;

wherein said topical composition is a leave-on composition.

2. A topical composition according to claim 1 wherein the phenolic compound is selected from the group comprising phenolic acids, flavonoids, or isoflavonoids, or derivatives thereof or mixtures thereof.

3. A topical composition according to claim 1 wherein the phenolic compound is epigallocatechin gallate, naringenin, quercitin, catechin, daidzein, genistein, lycetin, gallic acid, or a green tea phenol.

4. A topical skin care composition comprising:

(a) a petroselinic acid compound which is coriander seed oil;

(b) a phenolic compound selected from the group consisting of soy extract, green tea extract, and mixtures thereof; and (c) a cosmetically acceptable vehicle;

wherein said topical composition is a leave on composition.

5. The skin care composition of claim 4, wherein said phenolic compound is soy extract.

6. The skin care composition of claim 1, wherein said phenolic compound is selected from the group consisting of epigallocatechin gallate (EGCG), quercetin, daidzein, gallic acid, genistein, and mixtures thereof.

7. The skin care composition of claim 1, wherein said phenolic compound is selected from the group consisting of epigallocatechin gallate (EGCG), quercetin, genistein, and mixtures thereof.

* * * * *